United States Patent
Jin et al.

(10) Patent No.: US 12,285,335 B2
(45) Date of Patent: Apr. 29, 2025

(54) SPLIT TYPE PRECISELY-ANCHORABLE INTERVENTIONAL AORTIC VALVE SYSTEM

(71) Applicant: BEIJING BALANCE MEDICAL TECHNOLOGY CO., LTD., Beijing (CN)

(72) Inventors: Lei Jin, Beijing (CN); Xiangbin Pan, Beijing (CN); Jia Wu, Beijing (CN); Liyan Li, Beijing (CN); Zhihao Fan, Beijing (CN); Kangjian Wu, Beijing (CN)

(73) Assignee: BEIJING BALANCE MEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 18/710,518

(22) PCT Filed: Nov. 17, 2022

(86) PCT No.: PCT/CN2022/132631
§ 371 (c)(1),
(2) Date: May 15, 2024

(87) PCT Pub. No.: WO2023/088384
PCT Pub. Date: May 25, 2023

(65) Prior Publication Data
US 2025/0032252 A1 Jan. 30, 2025

(30) Foreign Application Priority Data
Nov. 17, 2021 (CN) .......................... 202111360380.6

(51) Int. Cl.
*A61F 2/24* (2006.01)
*A61F 2/95* (2013.01)

(52) U.S. Cl.
CPC .......... *A61F 2/2433* (2013.01); *A61F 2/2418* (2013.01); *A61F 2/95* (2013.01);
(Continued)

(58) Field of Classification Search
CPC ........ A61F 2/2433; A61F 2/2418; A61F 2/95; A61F 2220/0008; A61F 2230/0069;
(Continued)

(56) References Cited

U.S. PATENT DOCUMENTS

2007/0208550 A1\* 9/2007 Cao .......................... G06F 30/23
703/11
2007/0244552 A1 10/2007 Salahieh et al.
(Continued)

FOREIGN PATENT DOCUMENTS

| CN | 103300944 A | 9/2013 |
| CN | 203483543 U | 3/2014 |

(Continued)

OTHER PUBLICATIONS

First of office action of prior Chinese application No. 202211461848.5 dated Jun. 27, 2023.
(Continued)

*Primary Examiner* — Suzette J Gherbi
(74) *Attorney, Agent, or Firm* — Outlier Patent Attorneys, PLLC

(57) ABSTRACT

A split type precisely-anchorable transcatheter aortic valve system comprises a split transcatheter aortic valve anchoring stent (10) and a transcatheter artificial biological aortic valve (20), wherein the shape and structure of the transcatheter aortic valve anchoring stent (10) are matched with the real structure of the aortic valve after the patient's image data is subjected to three-dimensional reconstruction, the transcatheter aortic valve anchoring stent (10) is delivered to the aortic valve position of the patient to be released, deformed
(Continued)

and combined with the aortic valve leaflet tissue and the subvalvular tissue of the patient; the transcatheter artificial biological aortic valve (20) is delivered into the transcatheter aortic valve anchoring stent (10) to be released, the valve stent is deformed to expand the valve to the functional state, the transcatheter aortic valve anchoring stent (10) is deformed again and combined with the expanded transcatheter artificial biological aortic valve (20), and meanwhile, the transcatheter aortic valve anchoring stent (10) is deformed and anchored again. A system designed based on three-dimensional reconstruction can realize accurate anchoring of transcatheter aortic valve personalization.

21 Claims, 11 Drawing Sheets

(52) U.S. Cl.
CPC ............... *A61F 2220/0008* (2013.01); *A61F 2230/0069* (2013.01); *A61F 2230/0093* (2013.01); *A61F 2250/0004* (2013.01); *A61F 2250/0039* (2013.01); *A61F 2250/006* (2013.01)

(58) Field of Classification Search
CPC ...... A61F 2230/0093; A61F 2250/0004; A61F 2250/0039; A61F 2250/006; A61F 2/2409; A61F 2230/0054; A61F 2230/0067; A61F 2/2436; A61F 2/24
See application file for complete search history.

(56) References Cited

U.S. PATENT DOCUMENTS

| | | | |
|---|---|---|---|
| 2009/0005863 A1 | 1/2009 | Goetz et al. | |
| 2013/0289391 A1 | 10/2013 | Levy et al. | |
| 2016/0303804 A1* | 10/2016 | Grbic | G06T 19/00 |
| 2017/0057169 A1 | 3/2017 | Grbic et al. | |
| 2017/0069131 A1 | 3/2017 | Grbic et al. | |
| 2018/0338832 A1 | 11/2018 | Ganesan et al. | |
| 2020/0046530 A1* | 2/2020 | Goetz | A61F 2/95 |
| 2024/0238083 A1* | 7/2024 | Figulla | A61F 2/2418 |
| 2025/0025299 A1* | 1/2025 | Kyne | A61F 2/2418 |

FOREIGN PATENT DOCUMENTS

| | | |
|---|---|---|
| CN | 107405194 A | 11/2017 |
| CN | 107496054 A | 12/2017 |
| CN | 107496056 A | 12/2017 |
| CN | 111227931 A | 6/2020 |
| CN | 111284000 A | 6/2020 |

OTHER PUBLICATIONS

First search report of prior application No. 202211461848.5.
International Search Report of PCT/CN2022/132631 dated Jan. 18, 2023.
Rejection of prior Chinese application No. 202211461848.5 dated Oct. 27, 2023.
Reexamination Decision of prior Chinese application No. 202211461848.5 dated Mar. 4, 2024.
Second office action of prior Chinese application No. 202211461848.5 dated May 9, 2024.

* cited by examiner

SPLIT TYPE PRECISELY-ANCHORABLE INTERVENTIONAL AORTIC VALVE SYSTEM

CROSS-REFERENCE TO RELATED APPLICATIONS

This application claims priority to International Application No. PCT/CN2022/132631, filed on Nov. 17, 2022, which claims the priority benefit of China Patent Application No. 202111360380.6, filed on Nov. 17, 2021. The contents of the above identified applications are incorporated herein by reference in their entirety.

TECHNICAL FIELD

The application relates to an artificial biological heart valve, in particular to a split type precisely-anchorable transcatheter aortic valve system.

BACKGROUND ART

The development and clinical application of the transcatheter aortic valve (TARV) has been 20 years. Due to the advantages of minimally invasive surgery, no need for extracorporeal circulation, the near- and medium-term effects are accurate, it has been recognized as an effective treatment for patients at high-risk of old age or traditional surgical aortic valve replacement. At present, 65 countries in the world, 1,400 hospitals have carried out transcatheter aortic valve (TAVR) surgery, with a total of more than 600,000 transcatheter aortic valves (FIG. 1), an annual increase of 40%, and 182,000 TAVR surgeries worldwide in 2021. In 65 countries around the world, 1,400 hospitals have carried out transcatheter aortic valve (TAVR) surgery, with a total of more than 600,000 transcatheter aortic valves (FIG. 1), an annual increase of 40%, and 182,000 TAVR surgeries worldwide in 2021. However, for some patients with severe calcification of the two-leaflet aortic valve, ascending aortic dilatation, coronary artery occlusion risk and simple aortic regurgitation (AR), existing TAVR products do not meet the treatment needs of such patients, even in patients with severe stenosis at the aortic valve are often accompanied by the occurrence of various serious complications, such as valve regurgitation or valve displacement or even detachment caused by valve deformation after released, coronary opening obstruction, severe perivalvular leakage, conduction block caused by compression and injury of the sinoatrial node, and rupture or even death of the valve ring caused by excessive expansion of the valve. The existence of these complications not only put patients at risk, but also increase the difficulty of mastering skills and need to accumulate experience for a long time, if the transcatheter aortic valve is released in vivo to ensure accurate and stable anchoring, the above problems are expected to be solved.

SUMMARY

For this purpose, the transcatheter aortic valve system of the present application provides a split design based on the anatomical structure of the real lesion of the aortic valve after the personalized image data of the patient is subjected to three-dimensional reconstruction, comprises two parts of a transcatheter aortic valve anchoring stent and a transcatheter artificial biological aortic valve, firstly intervenes a specific stent to clamp the valve leaflet, and then the transcatheter artificial biological aortic valve is introduced into the stent to be released, so that the transcatheter artificial biological aortic valve and the anchoring stent are combined into a whole, and accurate preset anchoring is achieved.

The application relates to a split type precisely-anchorable transcatheter aortic valve system, which comprises a split transcatheter aortic valve anchoring stent and a catheter intervention artificial biological aortic valve prosthesis and a corresponding delivery system and kit. The shape and structural design of the transcatheter aortic valve anchoring stent are matched with the real structure of the lesion aortic valve after three-dimensional reconstruction according to the patient's image data, the transcatheter aortic valve anchoring stent is delivered to the aortic valve position of the patient through the catheter, the anchoring wire loop, the stent connecting structure and the inflow surface lattice of the aortic valve anchoring stent are sequentially released, so that each part of the aortic valve anchoring stent is clamped with the aortic valve outflow surface and the inflow surface of the patient to form a clamp up and down, and the original function of the aortic valve of the lesion is maintained, and the transcatheter artificial biological aortic valve which is input through the catheter is smoothly guided into the stent inner deployment passage, namely the first state of the aortic valve anchoring stent; the transcatheter artificial biological aortic valve is pressed, loaded and sent to the aortic valve anchoring stent in the first state of the previous intervention through the delivery device catheter, the transcatheter artificial biological aortic valve (or the nickel-titanium memory alloy stent self-expansion) is assisted by the balloon dilation, the aortic valve anchoring stent is deformed into a cylindrical second anchoring state as the transcatheter artificial biological aortic valve is expanded, and the anchoring stent and the transcatheter artificial biological aortic valve are embedded and integrated, and meanwhile, the anchoring wire loops or lattices at the two ends of the anchoring stent in the second state are tightly combined with the aortic valve leaflet and the subvalvular tissue, so that transcatheter treatment of the whole indication (narrow or regurgitation and narrow combined reflux) of the lesion patient's aortic valve is achieved.

The technical solution and the implementation process of the present application are as follows.

The split type precisely-anchorable transcatheter aortic valve system comprises a split transcatheter aortic valve anchoring stent and a transcatheter artificial biological aortic valve. ① The shape and structural design of the transcatheter aortic valve anchoring stent is based on CT and ultrasound image data of the aortic valve position of the patient, and the three-dimensional aortic valve real anatomical structure and shape are reconstructed by introducing proprietary software, so that the transcatheter aortic valve anchoring stent is designed, laser cutting, three-dimensional forming, heat treatment and polishing are performed to prepare the first state of the transcatheter aortic valve anchoring stent, and it is cleaned, packaged, and disinfected for future use. ② Use the loader to hold the loading anchor stent and deliver it to the patient's aortic valve position for positioning and releasing, and the stent deformation presents the first anchoring state in alignment and combination with the patient's aortic valve leaflets and the subvalvular tissue. ③ The transcatheter artificial biological aortic valve loading and delivery device is subsequently delivered into the transcatheter aortic valve anchoring stent to be released, the transcatheter artificial biological aortic valve is expanded to a functional state by the balloon expandable external force, the aortic valve anchoring stent is also deformed again to be embedded and combined with the expanded transcatheter artificial biological aortic valve, and the aortic valve anchoring stent deforms again to the second anchoring state and completes anchoring with leaflet tissue to achieve final preset anchoring.

Further, The split type precisely-anchorable transcatheter aortic valve system further comprises a delivery assembly, wherein the delivery assembly comprises a transcatheter artificial biological aortic valve anchoring stent delivery set and a transcatheter artificial biological aortic valve delivery set, and the transcatheter artificial biological aortic valve anchoring stent delivery set comprises a delivery catheter and a transcatheter artificial biological aortic valve anchoring stent loader.

The aortic valve anchoring stent has a compressed state disposed in the catheter, a first anchoring state after being released by the catheter, and a second anchoring state after being combined with the transcatheter artificial biological aortic valve, and in the first anchoring state, the aortic valve anchoring stent is released by the delivery device and then deformed to be in alignment engagement with the patient's aortic valve leaflet and the subvalvular tissue of the corresponding inflow surface; and in the second anchoring state, the aortic valve anchoring stent is undergoes secondary deformation via a transcatheter artificial biological aortic valve expansion, and combines with the transcatheter artificial biological aortic valve to complete the final anchoring and binding with patient's aortic valvular tissue. The real structure of the three-dimensional reconstruction is a digital image model or a three-dimensional printed simulation entity model. The anatomical structure of the simulated aortic valve lesion three-dimensionally reconstructed according to the patient's image data is a simulated three-dimensional image model and a simulation entity model of the corresponding three-dimensional printing after digital conversion of the integrated image of the patient's CT, the ultrasonic and the nuclear magnetic. The aortic valve anchoring stent is an umbrella tubular stent structure comprising a leaflet outflow surface, a leaflet inflow surface and a connecting part therebetween, and the leaflet outflow surface comprises two or three anchoring wire loops matching a real shape of three-dimensional reconstruction of the image data of the outflow surface of the patient's leaflet; the leaflet inflow surface of the anchoring stent is an anchoring wire loop corresponding to the wire loop of the outflow surface, which can form a structure that clamps the leaflets with the anchoring wire loop of the outflow surface, and the shape matches the real shape of the three-dimensional reconstruction of the aortic valve subvalvular image data; the connecting part of the anchoring stent is a circular funnel-shaped lattice, and the formed circumferential inner diameter matches the outer diameter after release of the transcatheter artificial biological aortic valve stent. The leaflet outflow surface is a telecentric outflow end, the leaflet inflow surface is a proximal inflow end, the anchoring wire loop at the outflow end is a quasi-circular folding type of a lattice extension of the stent connecting part, and the shape, size, and folding angle of the anchoring wire loop at the outflow end are matched with a lesion simulation shape according to three-dimensional reconstruction of the patient's image data; the anchoring wire loop at the inflow end of the stent is a quasi-circular small folding or a row of rhombic lattice structure, and the shape, size, and folding or row of rhombic lattice structure of the circular folding shape of the inflow end match the simulation shape and the peripheral diameter of the bottom of the aortic valve inflow end leaflet three-dimensionally reconstructed according of the patient's image data; the stent connecting part is a conical funnel-shaped lattice or three support rods connecting the inflow end and the outflow end, and the former taper matches the aortic valve simulation shape three-dimensionally reconstructed according to the patient's image data; and the actual length of the stent connection is measured from the lower edge of the coronary opening in the patient's image to the bottom of the valve base at the inflow end of the aortic valve. In that, in the first anchoring state, after the transcatheter aortic valve anchoring stent is released through the catheter, the transcatheter aortic valve anchoring stent is returned from the compressed state, the anchoring wire loop at the outflow end of the stent is folded back and folded back to correspondingly extend into the annulus of the lesion aortic valve leaflet of the patient and the quasi-circular small anchoring wire loop corresponding to the inflow end of the stent is everted out of the bottom of the leaflet base of the inflow end of the lesion aortic valve, the corresponding wire loops at the two ends form an alignment clamping between the inner and outer surfaces of the leaflet, and the lattice of the connecting part of the aortic valve anchoring stent is released to be funnel-shaped at the intersection of the lesion aortic valve leaflets, so that the leaflet is in an approximately normal open-close state; in the second anchoring state, in the first anchoring state, the transcatheter artificial biological aortic valve crimped into the strip is pressed into the stent through the catheter to enter the stent to be released by the balloon dilation, and the external force of the balloon dilation causes the transcatheter artificial biological aortic valve to expand from the strip to the cylindrical shape (functional state); and meanwhile, the anchoring stent undergoes a secondary deformation from a funnel-shaped shape to a cylindrical shape, which is tightly combined with the transcatheter artificial biological aortic valve, and as a result, the secondary deformation of the transcatheter aortic valve anchoring stent also re-anchors with the patient's lesion aortic valve leaflet and the root tissue of the leaflet attached to the aortic wall.

The outflow surface and the inflow surface of the connecting part of the aortic valve anchoring stent are both provided with a fixed support rod or stent end bending for embedding in the transcatheter artificial biological aortic valve stent, the direction of the fixed support rod or stent end bending is axis bending, and when which is deformed to cylindrical in the second state, the distance between the fixed support rod or stent end bending at the two ends of the outflow surface and inflow surface of the connecting part of the aortic valve anchoring stent is matched with the height of the transcatheter artificial biological aortic valve stent. The two ends of the connecting part of the aortic valve anchoring stent are provided for embedding a plurality of end centripetal hooks of the outflow end of the transcatheter artificial biological aortic valve stent, and the inflow end of the connecting part of the centripetal hooks and the aortic valve anchoring stent is provided with a plurality of fixed support rods or stent bending for embedding the inflow end of the transcatheter artificial biological aortic valve stent surrounding up and down, thereby preventing displacement of the transcatheter artificial biological aortic valve. The fixed support rod or stent bending is 3-12, preferably 3-6. The lattice of the connecting part of the aortic valve anchoring stent is a unit lattice composed of a compressible diamond lattice, a V-shaped lattice and/or a hexagonal or polygonal lattice, and the lattice portion is adaptively connected to the anchoring wire loops at both ends. The outer peripheral edge of the arc of the inflow end anchoring wire loop of the aortic valve anchoring stent is closely attached to the lower root of the patient's aortic valve. The second state of the aortic valve anchoring stent connecting part is cylindrical with an inner peripheral diameter matched with the outer diameters of various corresponding size specifications of the transcatheter artificial biological aortic valve. The surface of the aortic valve anchoring stent is coated with a layer of medical polymer film. The aortic valve anchoring stent is a three-dimensional forming structure or a separate connecting structure after laser integrated cutting. The anchor stent is made of a nickel-titanium alloy material.

The transcatheter artificial biological aortic valve of the present application comprises a cobalt-chromium alloy stent which is radially compressible and can be expanded by a balloon dilation and is cylindrical, or a nickel-titanium alloy stent which is radially compressible and self-expanding and is cylindrical, and three fan-shaped leaflets arranged on the inner side of the stent, wherein the three fan-shaped leaflets each have a free edge, an arc-shaped bottom edge and leaflet boundary connecting parts which extend on the two sides, and the stent is a metal net tube. The valve frame is a cobalt-based alloy cobalt or chromium alloy or a nickel-titanium alloy. The transcatheter aortic valve anchoring stent is firstly inserted into the lesion aortic valve position through the transcatheter aortic valve anchoring stent delivery catheter and released into the first anchoring state, and then the transcatheter artificial biological aortic valve is sent to the anchoring stent through the transcatheter artificial biological aortic valve delivery device catheter, and as the transcatheter artificial biological aortic valve is expanded, the transcatheter aortic valve anchoring stent is expanded to the second anchoring state, and finally, the fitting of the stent binding portion and the transcatheter artificial biological aortic valve and the stent deformation are in the second state, and further tight combination with the perivalvular and subvalvular tissue is completed to form the final anchoring. The transcatheter artificial biological aortic valve delivery kit comprises a transcatheter artificial biological aortic valve delivery device, a guide sheath, a transcatheter artificial biological aortic valve holder, and a charging pump.

The system of the present application is inserted through the femoral artery, carotid artery, subclavian artery, or apical puncture, and the transcatheter aortic valve anchoring stent and the transcatheter artificial biological aortic valve can be inserted through same pathway before and after, or through different pathways sequentially. Each time a personalized treatment process for specific patients is completed to achieve precise anchoring of the transcatheter artificial biological aortic valve, all relevant data mentioned above are treated as independent data units, accumulating a large amount of personalized data, and through artificial intelligence, the intelligent, large-scale, and industrialized implementation of the split type precisely-anchorable transcatheter aortic valve system is achieved.

DETAILED DESCRIPTION

Figure 1:
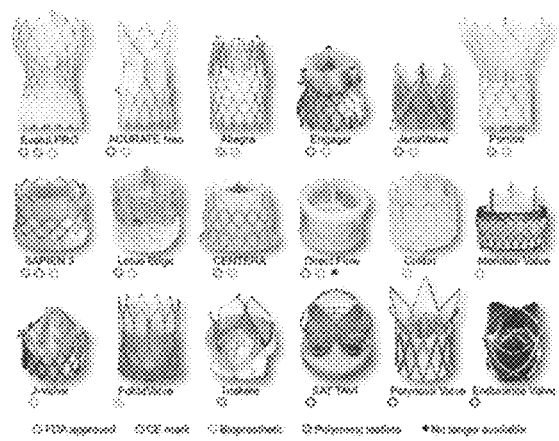
FIG. 1 is a schematic diagram of various integrated aortic valves in the prior art.
Figure 2A:
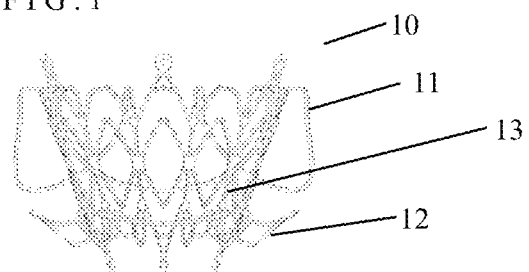
FIGS. 2A-C are schematic diagrams of anchor stents in different forms according to an embodiment of the present application.
Figure 2B:
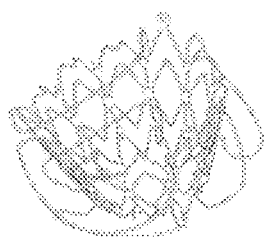
Figure 2C:
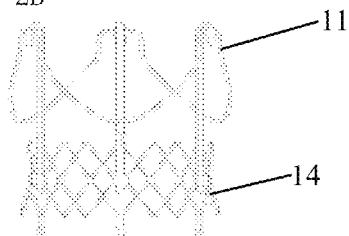
Figure 3A:
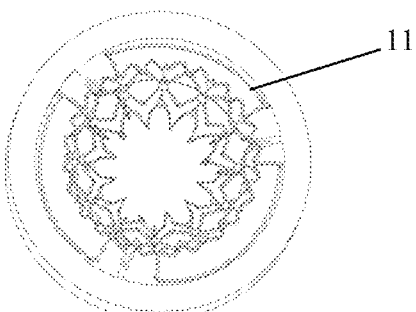
FIGS. 3A-B are schematic views of an anchoring stent outflow surface and an inflow surface according to an embodiment of the present application.
Figure 3B:
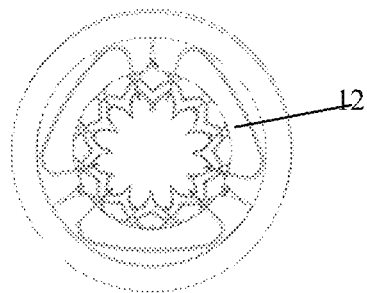

The split type precisely-anchorable transcatheter aortic valve system in the present embodiment comprises a split transcatheter aortic valve anchoring stent 10 and a transcatheter artificial biological aortic valve 20, wherein the shape and structure of the transcatheter aortic valve anchoring stent are matched with the real structure of the aortic valve after the personalized image data of the patient is subjected to three-dimensional reconstruction, the transcatheter aortic valve anchoring stent is delivered to the aortic valve position of the patient to be released, deformed and combined with the aortic valve leaflet and the subvalvular tissue of the patient; the transcatheter artificial biological aortic valve is delivered into the transcatheter aortic valve anchoring stent to be released, the transcatheter artificial biological aortic valve is deformed to expand the transcatheter artificial biological aortic valve to the functional state, the aortic valve anchoring stent is deformed again and combined with the expanded transcatheter artificial biological aortic valve, and the aortic valve anchoring stent is deformed and anchored again.

Referring to FIGS. 2-5, the transcatheter aortic valve anchoring stent of the present embodiment is one of the key components of the split type precisely-anchorable transcatheter aortic valve system of the present application. The stent is made of nickel-titanium alloy, the aortic valve anchoring stent is an umbrella tubular stent structure, and consists of three parts: ① a stent outflow surface anchoring wire loop 11; ② a stent inflow face anchoring wire loop 12 or an anchoring lattice 14; and ③ a stent connecting part 13. The leaflet outflow surface comprises two or three outflow surface anchoring wire loops, which is matched with the real shape of three-dimensional reconstruction of the image data of the outflow surface of the patient's leaflet; the leaflet inflow surface of the anchoring stent is a structure corresponding to the outflow surface anchoring wire loop, and can form a structure that clamps the leaflet 30 with the outflow surface anchoring wire loop, and the shape of the anchoring stent is matched with the real shape of the three-dimensional reconstruction of the aortic valve subvalvular image data; the connecting part of the anchoring stent is a circular funnel-shaped lattice, and the formed circumferential inner diameter is matched with the outer diameter after the intervention aortic valve stent is released. The lattice of the connecting part of the aortic valve anchoring stent is a unit lattice composed of a compressible diamond lattice, a V-shaped lattice and/or a hexagonal or polygonal lattice, and the lattice portion is adaptively connected to the anchoring wire loops at both ends. Because the outflow surface anchoring wire loop is matched with the real shape of the three-dimensional reconstruction of the image data of the outflow surface of the patient leaflet and the three-dimensional reconstruction of the aortic valve subvalvular image data, based on the same design principle and concept, the specific form and structure of the anchoring wire loop are slightly different, as shown in the figure, more accurate personalized design and adaptation are achieved, and better postoperative effect is achieved.

Figure 4A:
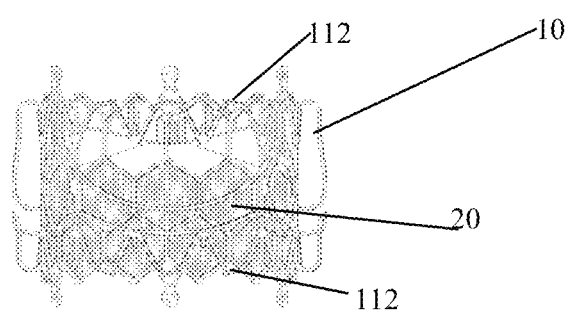
FIGS. 4A-C are schematic illustrations of an anchor stent and aortic valve binding according to an embodiment of the present application.
Figure 4B:
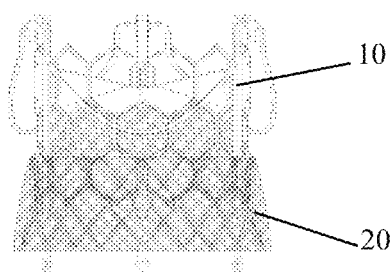
Figure 4C:
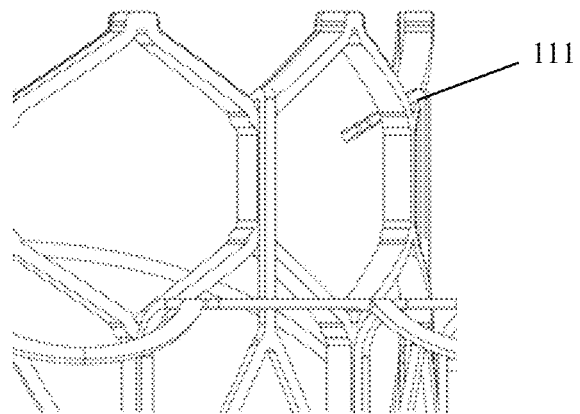
Figure 5A:
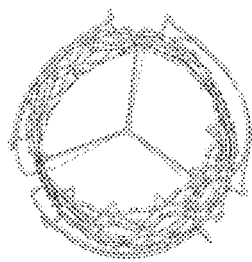
FIGS. 5A-B are schematic diagrams of outflow surfaces and inflow surfaces after an anchor stent and an aortic valve are joined according to an embodiment of the present application.
Figure 5B:
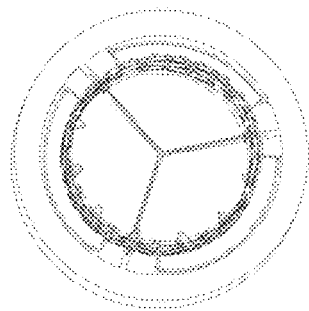

The outflow surface and the inflow surface of the connecting part of the aortic valve anchoring stent are both provided with a fixed support rod 111 or stent end bending 112 (referring to a partial enlarged schematic diagram in the form of a fixed support rod of FIG. 4C) for embedding in the transcatheter artificial biological aortic valve stent, the direction of the fixed support rod or stent end bending is axis bending, and when which is deformed to cylindrical in the second state, the distance between the fixed support rod or stent end bending at the two ends of the outflow surface and inflow surface of the connecting part of the aortic valve anchoring stent is matched with the height of the transcatheter artificial biological aortic valve stent. The two ends of the connecting part of the aortic valve anchoring stent are provided for embedding a plurality of end centripetal hooks of the outflow end of the transcatheter artificial biological aortic valve stent, and the inflow end of the connecting part of the centripetal hooks and the aortic valve anchoring stent is provided with a plurality of fixed support rods or stent bending for embedding the inflow end of the transcatheter artificial biological aortic valve stent surrounding up and down, thereby preventing displacement of the transcatheter artificial biological aortic valve. The fixed support rod or stent bending is 3-12, preferably 3-6. The outer peripheral edge of the arc of the inflow end anchoring wire loop of the aortic valve anchoring stent is 1-2 mm apart from the patient's aortic valve subvalvular lower root, preferably 1.5 mm apart. The second state of the aortic valve anchoring stent connecting part is cylindrical with an inner peripheral diameter matched with the outer diameters of various corresponding size specifications of the transcatheter artificial biological aortic valve. The surface of the aortic valve anchoring stent is coated with a layer of medical polymer film.

The transcatheter artificial biological aortic valve comprises a cobalt-chromium alloy stent which is radially compressible and can be expanded by a balloon dilation and is cylindrical, or a nickel-titanium alloy stent which is radially compressible and self-expanding and is cylindrical, and three fan-shaped leaflets arranged on the inner side of the stent, wherein the three fan-shaped leaflets each have a free edge, an arc-shaped bottom edge and leaflet boundary connecting parts which extend on the two sides, and the stent is a metal net tube. It is similar to structures well known in the art.

The number, shape, size, and curvature of the anchoring wire loops on the outflow and inflow surfaces of the transcatheter aortic valve anchoring stent are matched with the preoperative CT image data of the patient's lesion aortic valve, and the real structure after three-dimensional reconstruction (3mensio), as well as the real size of each diameter item measured in the image, to create a processing drawing for the interventional aortic valve anchoring stent, and through specific nickel titanium memory alloy tube three-dimensional laser cutting and three-dimensional forming processing, the personalized interventional aortic valve anchoring stent is finally customized. The normal aortic valve is a three-leaflet structure, and due to the birth defect, t patients with bicuspid malformations, as well as elderly degenerative diseases, may develop valve calcification and rheumatic aortic valve disease. The shape of various types of aortic valve lesions matches the real structure of the aortic valve after three-dimensional reconstruction of imaging data.

Figure 6A:
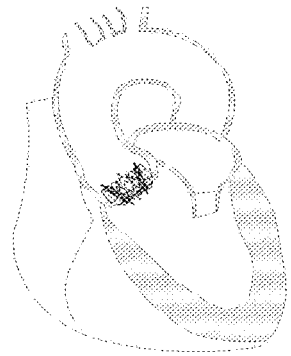
FIGS. 6A-B are schematic diagrams of a first anchoring state of a transcatheter aortic valve anchoring stent after being released by a catheter according to an embodiment of the present disclosure.
Figure 6B:
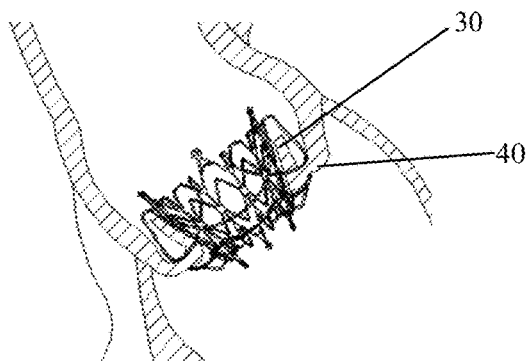
Figure 7A:
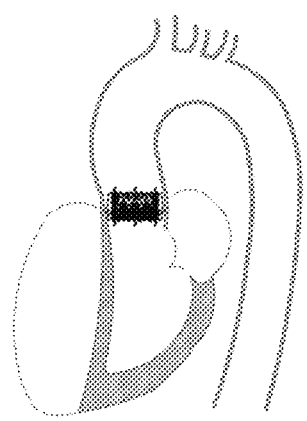
FIGS. 7A-B are schematic views of a second anchoring state after a transcatheter artificial biological aortic valve is delivered into an anchoring stent via a catheter according to an embodiment of the present application.
Figure 7B:
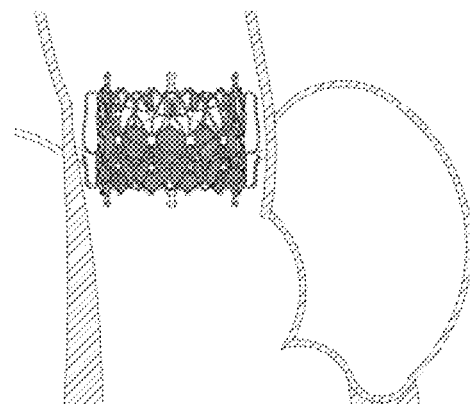
Figure 8:
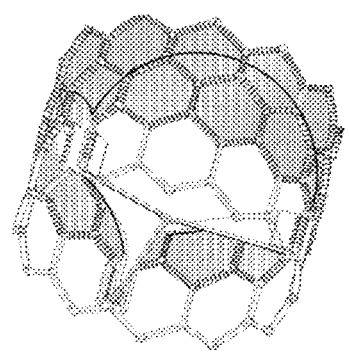
FIG. 8 is a schematic diagram of a transcatheter artificial biological aortic valve according to an embodiment of the present application.

The above processing and manufacturing of aortic valve anchoring stent based on patient imaging real data is the pre-gripping state of the stent, and it is also the first anchoring state after the stent is delivered to the aortic valve at the site of the lesion valve orifice through a delivery catheter and released (see FIG. 6). The second anchoring state of the transcatheter aortic valve anchoring stent is that when the transcatheter artificial biological aortic valve is delivered to the anchoring stent through the delivery catheter, and the transcatheter artificial biological aortic valve is dilated with the assistance of a balloon (or the nickel-titanium memory alloy aortic valve stent self-expands) to deform the transcatheter aortic valve anchoring stent from the first anchoring state to the second anchoring state, and the deformation force of the stent is integrated with the balloon expansion force released by the transcatheter artificial biological aortic valve (referring to FIG. 7), and meanwhile, the second state of the transcatheter aortic stent is tightly combined with the perivalvular and subvalvular tissue 40 to achieve final anchoring (FIG. 7B). Meanwhile, in the first anchoring state of the anchoring stent, the fixed support rods at the atrial end of the anchoring stent are deformed into the second anchoring state, the fixed support rods or stent bending ends at the two ends of the stent are bent towards the center to form axial parallelism, the resultant force of the bending ends of the fixed support rods or stents is buckled on the support rods at the two ends of the transcatheter artificial biological aortic valve stent, the anchoring stent is automatically interlocked with both ends of the transcatheter artificial biological aortic valve, so that the transcatheter artificial biological aortic valve and the anchoring stent are accurately combined into a whole, and the zero displacement of the transcatheter artificial biological aortic valve is ensured (see FIG. 4).

The application is summarized as follows: ① the split type transcatheter aortic valve system is composed of a transcatheter aortic valve anchoring stent and an intervening aortic valve and a delivery system and a system kit; ② the anchoring stent is formed by converting image data of a preoperative lesion aortic valve of a patient into a larger circular anchoring wire loop of the outflow surface of the three-dimensional real structural design anchoring stent and a smaller circular anchoring wire loop of the inflow surface, and the stent connecting structure between the two ends of the anchoring stent is a conical funnel-like lattice stent structure; ③ using the lesion aortic valve leaflet structure, designing an anchoring wire loop, accurately positioning and anchoring the outflow surface of the stent and the inflow surface wire loop; ④ the anchoring stent can release the first anchoring state through the femoral artery or the transapical approach in the aortic valve position, and the inner shape of the pathological aortic valve becomes the second anchoring state of the anchoring stent by means of the deformation force released by subsequent transcatheter artificial biological aortic valve expansion, so that the transcatheter artificial biological aortic valve can be automatically embedded and synthesized in the heart with the second anchoring state of the anchoring stent, and meanwhile, the perivalvular and subvalvular tissue fastening is completed to finish final anchoring again; and ⑤ the anchoring stent is deformed from the first state to the second state, the deformation process realizes automatic binding with the transcatheter artificial biological aortic valve, and the release control of the transcatheter artificial biological aortic valve can be automatically and accurately achieved.

Figure 9:
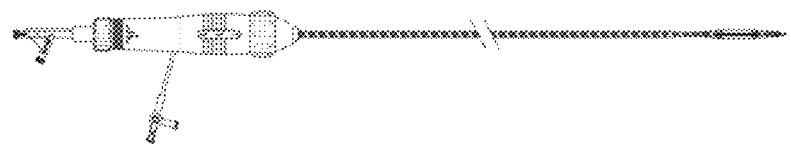
FIG. 9 is a schematic diagram of a transcatheter prosthetic aortic valve delivery system according to an embodiment of the present disclosure.
Figure 10:
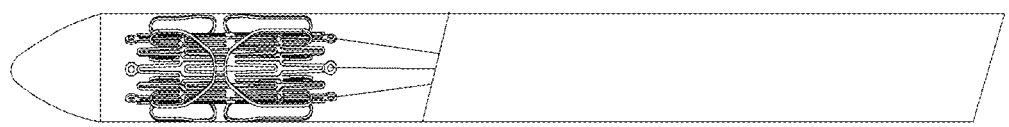
FIG. 10 is a schematic diagram of loading of a transcatheter aortic valve anchoring stent according to an embodiment of the present application.

Transcatheter Artificial Biological Aortic Valve and Delivery System and Implementation Referring to FIG. 9-10, a delivery system according to an embodiment of the present application includes a delivery catheter, a transcatheter aortic valve anchoring stent loader, a transcatheter artificial biological aortic valve holder, a valve release balloon, and a delivery device kit.

Figure 11A:
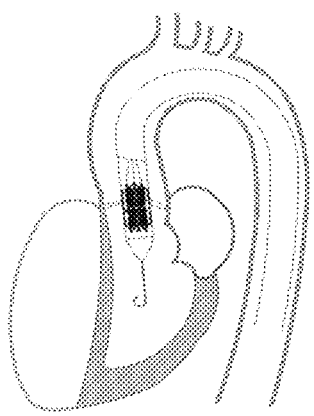
FIGS. 11A-C are schematic views of transfer of the aortic valve anchoring stent through the femoral artery according to an embodiment of the present application.
Figure 11B:
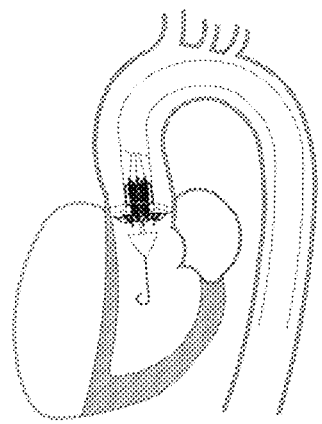
Figure 11C:
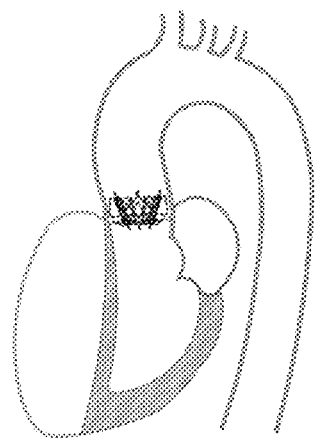
Figure 12A:
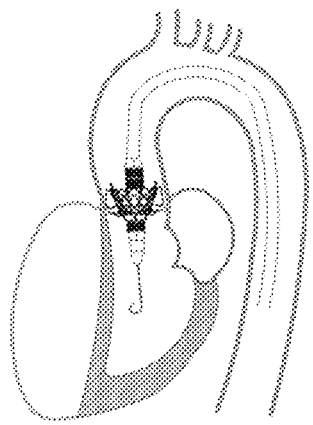
FIGS. 12A-C are schematic views of the anchoring stent shown in FIG. 11, which is inserted into the aortic valve through the femoral artery according to an embodiment of the present application.
Figure 12B:
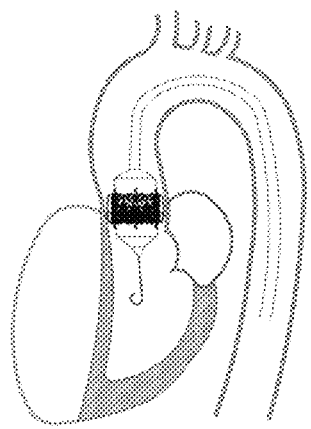
Figure 12C:
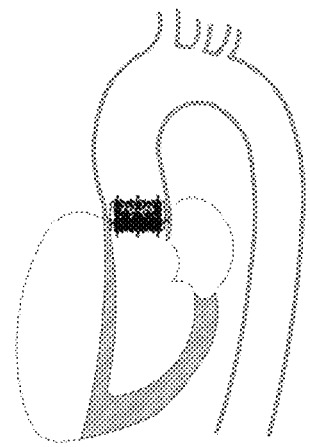

Referring to FIG. 11 to FIG. 12, in the first embodiment, the loaded anchoring stent is firstly delivered into the patient's aortic valve's lesion through the femoral artery (FIG. 11A), and the inflow surface and the outflow surface (FIG. 11B) of the anchoring stent are sequentially released, i.e., the first state of the anchoring stent (FIG. 11C). Referring to FIG. 12A-C, after the release of the anchor stent is completed, the delivery sheath is withdrawn, the pre-assembled transcatheter artificial biological aortic valve is delivered to the anchoring stent along the original path through the catheter (FIG. 12A), and then the transcatheter artificial biological aortic valve is assisted by balloon assistance, so that the anchoring stent is deformed into the second anchoring state (FIG. 12B), precise binding to the transcatheter artificial biological aortic valve is achieved, and meanwhile, the anchoring stent is buckled with the subvalvular tissue to complete final anchoring (FIG. 12C).

Figure 13A:
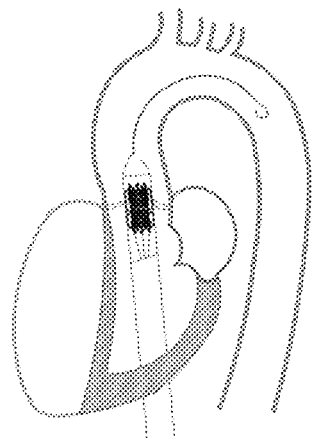
FIGS. 13A-C are schematic views of the transapical approach for implanting aortic valve anchoring stents according to an embodiment of the present application.
Figure 13B:
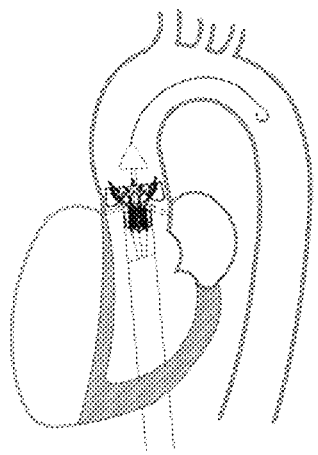
Figure 13C:
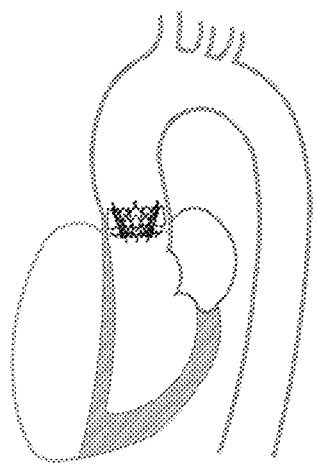
Figure 14A:
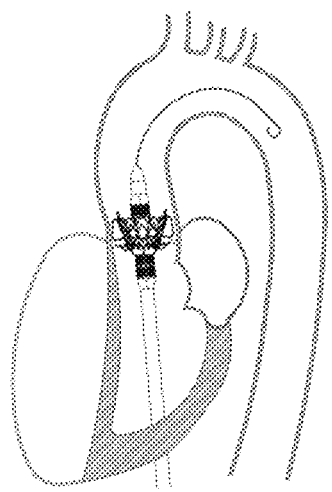
FIGS. 14A-C are schematic illustrations of the anchoring stent shown in FIG. 13, which is inserted into the aortic valve through the transapical approach according to an embodiment of the present application.
Figure 14B:
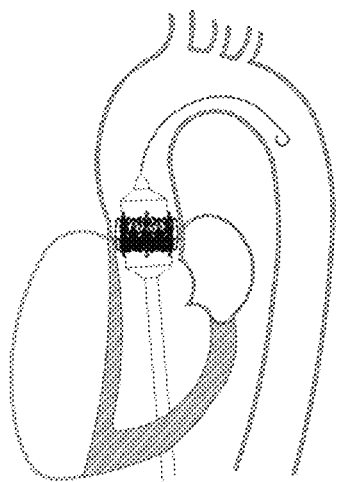
Figure 14C:
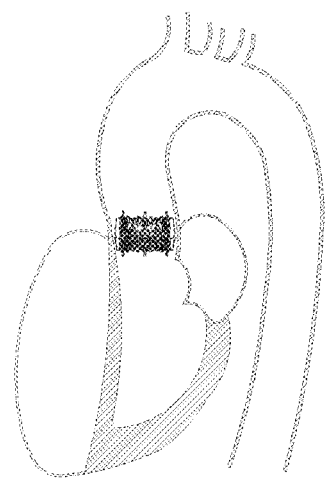
Figure 15A:
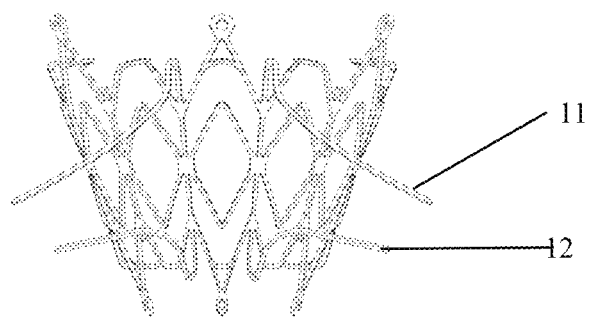
FIG. 15A-D is a schematic diagram of an anchoring stent for a two-leaflet patient according to an embodiment of the present disclosure.
Figure 15B:
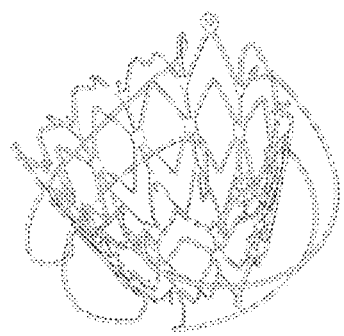
Figure 15C:
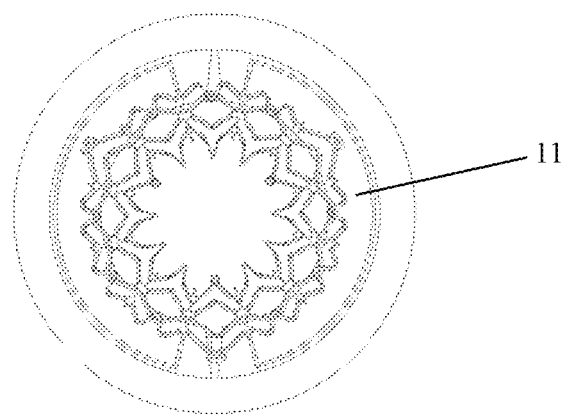
Figure 15D:
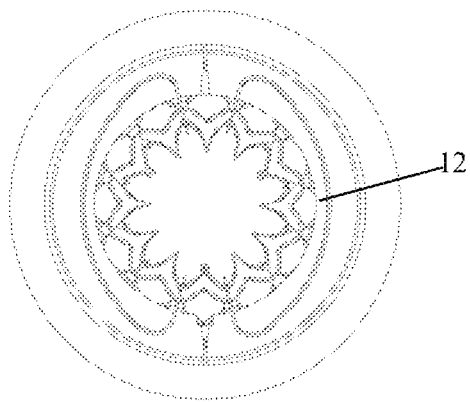

Referring to FIG. 13 to FIG. 14, in the second embodiment, the loaded anchoring stent is delivered into the aortic valve (FIG. 13A) of the lesion of the patient through the apical puncture, and the outflow surface (FIG. 13B) and the inflow surface of the anchoring stent are sequentially released, that is, the first state of the anchoring stent (FIG. 13C); after the release of the anchoring stent is completed, the transcatheter artificial biological aortic valve is pressed into the delivery sheath in advance, and the transcatheter artificial biological aortic valve is delivered into the anchoring stent through the transapical puncture (FIG. 14A), and then the transcatheter artificial biological aortic valve is assisted by balloon assistance, so that the anchoring stent is deformed into the second anchoring state (FIG. 14B), so that the anchoring stent is accurately combined with the transcatheter artificial biological aortic valve, and the final anchoring is completed simultaneously with the fastening of the perivalvular and subvalvular tissue (FIG. 14C).

In addition, there is also a transcatheter aortic valve anchoring stent of the two-leaflet patient, similar to the anchoring stent of the tri-leaflet patient, referring to FIG. 15, there are two anchoring wire loops in this embodiment.

Figure 16A:
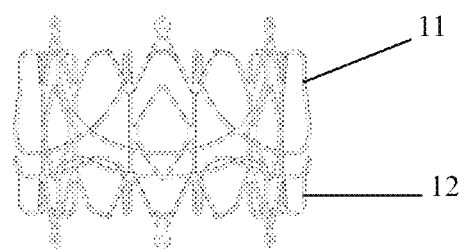
FIG. 16A-C is a schematic diagram of an anchor stent for patients with different lesions according to an embodiment of the present disclosure.
Figure 16B:
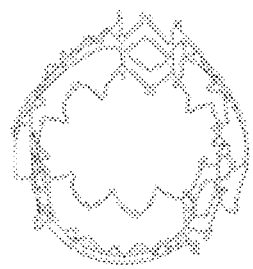
Figure 16C:
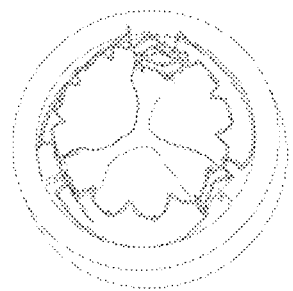

In some cases, the position of the aortic valve is very limited, and correspondingly, the lattice of the structure of the anchoring stent connecting part is also designed to be shorter, improving compatibility with perivalvular tissues, referring to FIG. 16.

The above embodiments are merely exemplary embodiments of the present application. The transcatheter aortic valve system of the present application has implemented the technical solutions described above in animal experiments, and confirmation is feasible.

The application can realize the significance that: ① the split type design realizes that the anchoring of the transcatheter artificial biological aortic valve and the support of the transcatheter artificial biological aortic valve stent on the valve leaflet are functionally separated, and the anchoring of the artificial biological aortic valve intervention to the aortic valve position is delivered to the anchoring stent, so that the anchor stent can be designed according to the real anatomical form and structure of the three-dimensional reconstruction of the specific image data of the patient, so that the anchoring is more accurate; the intervention of the anchoring stent and the intervention of the artificial biological aortic valve are involved stepwise, so that can avoid difficulties in conveying through catheters due to complex structures and large volumes that are difficult to grip; ② the second anchoring state of the anchoring stent can be preset by carrying out anchoring principle on the anatomical structural features of the lesion valve and the pre-design and measurement of the final anchoring part; the personalized image data of the patient, the special software and the three-dimensional printing pretest are used for constructing the size and dimension of each part of the anchoring stent to complete the preset, namely the three-dimensional shaping design and processing of the first anchoring state, so that the catheter is accurately aligned after being released, and the support is provided for smooth delivery of the transcatheter artificial biological aortic valve. For example, the conical structure of the first state of the anchoring stent can be moderately expanded and narrow, and can also be constrained more severely. The former not only provides a channel for artificial biological aortic valve intervention, but also can prevent the stenotic lesion from abruptly expanding; the latter can relieve a large amount of regurgitation of the transcatheter artificial biological aortic valve insufficiency, and provides space and time guarantee for the entry of the transcatheter artificial biological aortic valve; ③ the external force released by the transcatheter artificial biological aortic valve is used for driving the anchoring stent to be deformed from the first anchoring state to the second state, this deformation generates an anchoring stent to be tightly integrates with the transcatheter artificial biological aortic valve to ensure zero displacement of the transcatheter artificial biological aortic valve, and the inflow surface anchoring lattice or the hook loop structure is further tightly combined with the subvalvular tissue, so that the pre-designed alignment anchoring is realized, and meanwhile, the anchoring is completed with the structure on the valve;

④ the supporting rod structure which is arranged at the inflow end and the outflow end of the connecting part of the aortic valve anchoring stent can be integrated with the intervening aortic valve from both ends, so that the transcatheter artificial biological aortic valve is ensured to be free of displacement; ⑤ in the split-type precisely-anchorable transcatheter aortic valve system described above, each time a personalized and precise intervention for the aortic valve is completed, the analysis of relevant data, the shape design, processing and manufacturing of the transcatheter aortic valve anchoring stent, the relevant data obtained throughout the transcatheter treatment process, and postoperative follow-up data are used as independent data units to accumulate a large amount of personalized imaging data, anchoring stent design and processing and manufacturing parameters, transcatheter treatment process and postoperative results, and other related data, gradually realizing the intelligence, commercialization, and scale of the implementation of the split type precise anchoring interventional aortic valve system intervention treatment.

The invention claimed is:

1. A split type precisely-anchorable transcatheter artificial biological aortic valve system, characterized in that, the system comprises: a split transcatheter artificial biological aortic valve anchoring stent, and a transcatheter artificial biological aortic valve, and the transcatheter artificial biological aortic valve comprises a stent and three leaflets;

wherein, the shape and structure of the transcatheter artificial biological aortic valve anchoring stent are matched with a real structure of an aortic valve after three-dimensional reconstruction according to patient's image data, the transcatheter artificial biological aortic valve anchoring stent is delivered to the patient's aortic valve site for release, deformation alignment with the patient's aortic valve leaflet tissue and subvalvular tissue;

the transcatheter artificial biological aortic valve is delivered into the transcatheter artificial biological aortic valve anchoring stent for release, and the stent deforms and expands the transcatheter artificial biological aortic valve to a functional state, causing the transcatheter artificial biological aortic valve anchoring stent to deform again and be embedded with the expanded transcatheter artificial biological aortic valve, and meanwhile, the transcatheter artificial biological aortic valve anchoring stent deforms and anchors again;

the transcatheter artificial biological aortic valve anchoring stent has a compressed state disposed within a catheter, a first anchoring state after being released by the catheter, and a second anchoring state after being combined with the transcatheter artificial biological aortic valve; in the first anchoring state, the transcatheter artificial biological aortic valve anchoring stent is released and then deformed to be in alignment engagement with the patient's aortic valve leaflet and the subvalvular tissue of a corresponding inflow surface; and in the second anchoring state, the transcatheter artificial biological aortic valve anchoring stent undergoes secondary deformation via a transcatheter artificial biological aortic valve expansion, and combines with the transcatheter artificial biological aortic valve to complete final anchoring and binding with the patient's aortic valvular tissue;

the transcatheter artificial biological aortic valve anchoring stent's first anchoring state is an umbrella tubular stent structure comprising a leaflet outflow surface, a leaflet inflow surface and a stent connecting part therebetween; and the leaflet outflow surface is two or three anchoring wire loops matching a real shape of three-dimensional reconstruction of the image data of the outflow surface of the patient's leaflet; the leaflet inflow surface of the transcatheter artificial biological aortic valve anchoring stent is an anchoring wire loop corresponding to the anchoring wire loop of the leaflet outflow surface of the anchoring stent, which can form a structure that clamps the leaflets with the anchoring wire loop of the leaflet outflow surface of the anchoring stent, with a shape matching the real shape of the three-dimensional reconstruction of the aortic valve subvalvular image data; the stent connecting part of the transcatheter artificial biological aortic valve anchoring stent is a circular funnel-shaped lattice, an inner diameter of a formed circumference matches an outer diameter of the stent of the transcatheter artificial biological aortic valve after release;

the second anchoring state of the stent connecting part of the transcatheter artificial biological aortic valve anchoring stent is cylindrical with an inner peripheral diameter matched with the outer peripheral diameter of the transcatheter artificial biological aortic valve.

2. The split type precisely-anchorable transcatheter artificial biological aortic valve system according to claim 1, characterized in that, the aortic valve leaflet tissue is a leaflet and a leaflet root tissue of a valve inflow surface.

3. The split type precisely-anchorable transcatheter artificial biological aortic valve system according to claim 1, characterized in that, further comprising: a delivery assembly, wherein the delivery assembly comprises a transcatheter artificial biological aortic valve anchoring stent delivery kit and a transcatheter artificial biological aortic valve delivery kit; the transcatheter artificial biological aortic valve anchoring stent delivery kit comprises a delivery catheter and a transcatheter artificial biological aortic valve anchoring stent loader.

4. The split type precisely-anchorable transcatheter artificial biological aortic valve system according to claim 3, characterized in that the transcatheter artificial biological aortic valve is delivered into the transcatheter artificial biological aortic valve anchoring stent through a catheter for release, the stent deforms and expands the transcatheter artificial biological aortic valve to a functional state, causing the transcatheter artificial biological aortic valve anchoring stent to deform again and be embedded with the expanded transcatheter artificial biological aortic valve, and meanwhile, the transcatheter artificial biological aortic valve anchoring stent deforms again, causing the transcatheter artificial biological aortic valve anchoring stent combines again with the lesion leaflet and the subvalvular tissue, so that the transcatheter artificial biological aortic valve anchoring stent forms a clamping portion with the leaflet and the corresponding inflow surface subvalvular tissue, and while re-anchoring, the transcatheter artificial biological aortic valve combined with it is limited.

5. The split type precisely-anchorable transcatheter artificial biological aortic valve system according to claim 1, characterized in that, a real structure of the aortic valve reconstructed in three-dimensions according to the patient's image data is a digital image model or a three-dimensional printed simulation entity model.

6. The split type precisely-anchorable transcatheter artificial biological aortic valve system according to claim 5, characterized in that, a real structure of the aortic valve reconstructed in three-dimensions according to the patient's image data is an anatomical structure of a simulated aortic valve lesion, and its digital image model is a three-dimensional image model simulated by a comprehensive images digital conversion of CT, ultrasound, and MRI of the patient, and its simulated entity model is the corresponding 3D printed simulated entity model.

7. The split type precisely-anchorable transcatheter artificial biological aortic valve system according to claim 3, characterized in that, the leaflet outflow surface of the anchoring stent is a telecentric outflow end, the leaflet inflow surface of the anchoring stent is a proximal inflow end, the anchoring wire loop at the outflow end is a quasi-circular folding type of a lattice extension of the stent connecting part, and the shape, size, and folding angle of the anchoring wire loop at the outflow end are matched with a lesion simulation shape according to three-dimensional reconstruction of the patient's image data; the anchoring wire loop at the inflow end is a quasi-circular small folding or a row of rhombic lattice structure, and the shape, size, and folding or row of rhombic lattice structure of the circular small folding shape of the inflow end match the simulation shape and the peripheral diameter of the bottom of the aortic valve inflow end leaflet three-dimensionally reconstructed according of the patient's image data;

the stent connecting part is a conical funnel-shaped lattice or three support rods connecting the inflow end and the outflow end, and the former taper matches the aortic valve simulation shape three-dimensionally reconstructed according to the patient's image data; and an actual length from the lower edge of the coronary opening in the patient's image to the bottom of the valve base at the inflow end of the aortic valve is a length of the stent connecting part.

8. The split type precisely-anchorable transcatheter artificial biological aortic valve system according to claim 7, characterized in that, in the first anchoring state, after the transcatheter artificial biological aortic valve anchoring stent is released through the catheter, the transcatheter aortic valve anchoring stent is returned from the compressed state, the anchoring wire loop at the outflow end of the transcatheter artificial biological aortic valve anchoring stent is folded back to correspondingly extend to the annulus of the lesion aortic valve leaflet of the patient and the quasi-circular small folding's anchoring wire loop corresponding to the inflow end is everted out of the bottom of the leaflet base of the inflow end of the lesion aortic valve, the corresponding anchoring wire loops at the two ends form an alignment clamping inside and outside the leaflet as well as up and down, and the lattice of the connecting part of the transcatheter artificial biological aortic valve anchoring stent is released to be funnel-shaped at the intersection of the lesion aortic valve leaflets, so that the leaflet is in an approximately normal open-close state;

in the second anchoring state, the transcatheter artificial biological aortic valve delivered through the catheter and crimped into a strip shape in the first anchoring state enters the transcatheter artificial biological aortic valve anchoring stent to be released by the balloon dilation, and the external force of the balloon dilation causes the transcatheter artificial biological aortic valve to expand from the strip shape to a cylindrical-shape functional state; and meanwhile, the transcatheter artificial biological aortic valve anchoring stent undergoes a secondary deformation from a funnel-shaped shape to a cylindrical shape, which is tightly combined with the transcatheter artificial biological aortic valve, and as a result, the secondary deformation of the transcatheter artificial biological aortic valve anchoring stent also re-anchors with the patient's lesion aortic valve leaflet and the root tissue of the leaflet attached to the aortic wall.

9. The split type precisely-anchorable transcatheter artificial biological aortic valve system according to claim 1, characterized in that, the outflow surface and the inflow surface of the stent connecting part of the transcatheter artificial biological aortic valve anchoring stent are both provided with a fixed support rod or stent end bending for embedding in the stent of the transcatheter artificial biological aortic valve, the direction of the fixed support rod or stent end bending is axis bending, and when deformed to a cylindrical shape in the second anchoring state, the distance between the fixed support rod or stent end bending at the two ends of a leaflet outflow surface and a leaflet inflow surface of the stent connecting part of the transcatheter artificial biological aortic valve anchoring stent is matched with the height of the stent of the transcatheter artificial biological aortic valve.

10. The split type precisely-anchorable transcatheter artificial biological aortic valve system according to claim 9, characterized in that, the two ends of the stent connecting part of the transcatheter artificial biological aortic valve anchoring stent are provided with a plurality of end centripetal hooks for embedding the outflow end of the stent of the transcatheter artificial biological aortic valve; the centripetal hooks surround up and down with the plurality of fixed support rods or stent end bending provided at the inflow end of the stent connecting part of the transcatheter artificial biological aortic valve anchoring stent for embedding the inflow end of the transcatheter artificial biological aortic valve, thereby preventing displacement during the release of the transcatheter artificial biological aortic valve.

11. The split type precisely-anchorable transcatheter artificial biological aortic valve system according to claim 10, characterized in that, the number of the fixed support rod or stent end bending is 3-12.

12. The split type precisely-anchorable transcatheter artificial biological aortic valve system according to claim 1, characterized in that the stent connecting part of the transcatheter artificial biological aortic valve anchoring stent is a unit lattice composed of a compressible diamond lattice or a V-shaped lattice, and the stent connecting part is adaptively connected to the anchoring wire loops at both ends.

13. The split type precisely-anchorable transcatheter artificial biological aortic valve system according to claim 1, characterized in that, the outer peripheral edge of the arc of the inflow end anchoring wire loop of the transcatheter artificial biological aortic valve anchoring stent is closely attached to the lower root of the patient's aortic valve.

14. The split type precisely-anchorable transcatheter artificial biological aortic valve system according to claim 1, characterized in that, the surface of the transcatheter artificial biological aortic valve anchoring stent is coated with a layer of medical polymer film.

15. The split type precisely-anchorable transcatheter artificial biological aortic valve system according to claim 1, characterized in that, the transcatheter artificial biological aortic valve anchoring stent is a three-dimensional forming structure or a separate connecting structure after laser integrated cutting.

16. The split type precisely-anchorable transcatheter artificial biological aortic valve system according to claim 1, characterized in that, the transcatheter artificial biological aortic valve anchoring stent is made of a nickel-titanium alloy material.

17. The split type precisely-anchorable transcatheter artificial biological aortic valve system according to claim 3, characterized in that the stent comprises a cobalt-chromium alloy stent which is radially compressible and can be expanded to a cylindrical shape by a balloon dilation, or a nickel-titanium alloy stent which is radially compressible and self-expanding to a cylindrical shape; the three leaflets are three fan-shaped leaflets arranged on the inner side of the stent; the three leaflets each has a free edge, an arc-shaped bottom edge and leaflet boundary connecting parts which extend on the two sides, and the stent is a metal net tube.

18. The split type precisely-anchorable transcatheter artificial biological aortic valve system according to claim 17, characterized in that, the stent is a cobalt-based alloy cobalt or chromium alloy or a nickel-titanium alloy.

19. The split type precisely-anchorable transcatheter artificial biological aortic valve system according to claim 17, characterized in that, the transcatheter artificial biological aortic valve anchoring stent is firstly delivered into the lesion aortic valve position through a delivery catheter and released into the first anchoring state, and then the transcatheter artificial biological aortic valve is delivered to the transcatheter artificial biological aortic valve anchoring stent through a transcatheter artificial biological aortic valve delivery kit; as the transcatheter artificial biological aortic valve is expanded, the transcatheter artificial biological aortic valve anchoring stent is expanded to the second anchoring state fitting the transcatheter artificial biological aortic valve, and further tight combination with the perivalvular and subvalvular tissue is completed to form a final anchoring.

20. The split type precisely-anchorable transcatheter artificial biological aortic valve system of claim 4, characterized in that, the transcatheter artificial biological aortic valve delivery kit comprises a transcatheter artificial biological aortic valve delivery device, a guide sheath, a valve holder, and a charging pump.

21. The split type precisely-anchorable transcatheter artificial biological aortic valve system according to claim 1, characterized in that, the system is inserted through the femoral artery, carotid artery, subclavian artery, or apical puncture, and the transcatheter artificial biological aortic valve anchoring stent and the transcatheter artificial biological aortic valve can be inserted through the same pathway sequentially, or through different pathways sequentially.

* * * * *